United States Patent [19]

Nair et al.

[11] Patent Number: 5,260,296
[45] Date of Patent: Nov. 9, 1993

[54] THIOPHENE SUBSTITUTED ANTITUMOR ANTIFOLATES

[76] Inventors: Madhavan G. Nair, 7005 Charleston Oaks Dr. North; Ann Abraham, 6404 Glascow Ct., both of Mobile, Ala. 36695

[21] Appl. No.: 882,484

[22] Filed: May 13, 1992

[51] Int. Cl.$^5$ ............................................. A61K 31/505
[52] U.S. Cl. ..................................... 514/249; 544/260
[58] Field of Search ........................ 514/249; 544/260

[56] References Cited

U.S. PATENT DOCUMENTS

| | | | |
|---|---|---|---|
| 4,393,064 | 12/1983 | DeGraw | 514/249 |
| 4,746,659 | 5/1988 | DeGraw et al. | 514/249 |
| 4,882,234 | 11/1989 | Shih et al. | 514/258 |
| 4,920,125 | 4/1990 | Taylor et al. | 544/320 |
| 4,996,207 | 2/1991 | Nair | 544/260 |
| 5,028,608 | 7/1991 | Taylor et al. | 514/258 |
| 5,077,404 | 12/1991 | Piper et al. | 514/249 |
| 5,112,837 | 5/1992 | Burrows et al. | 546/176 |
| 5,167,963 | 12/1992 | DeGraw et al. | 544/260 |

FOREIGN PATENT DOCUMENTS 0318225  5/1989  European Pat. Off. .

OTHER PUBLICATIONS

DeGraw, et al. J. Med. Chem. 17, 552 (1974).
Nair, M. G. J. Org. Chem. 50, 1879, 1985.
P. R. Marsham, et al. J. Med. Chem. 34, 1594 (1991).

*Primary Examiner*—Donald G. Daus

[57] ABSTRACT

A new thiophene substituted antitumor antifolate, N{[5-(2,4-diamino-6-pteridinyl)ethyl]2-theonyl}-L-glutamic acid having the structural formula 1 is provided, as well as methods for its preparation. The new thiophene substituted antifolate 1 is a very potent inhibitor of the enzyme dihydrofolate reductase, undergoes moderate polyglutamylation and is transported to tumor cells more effectively than methotrexate. Compound 1 is an excellent inhibitor of tumor cells growth in culture, the potency being superior to methotrexate against CCRF-CEM human lukemia cells.

4 Claims, No Drawings

THIOPHENE SUBSTITUTED ANTITUMOR ANTIFOLATES

ORIGIN OF INVENTION

The invention described herein was in part made in the course of work under a grant from the National Institutes of Health, Department of Health, Education and Welfare.

BACKGROUND OF THE INVENTION

Field of the Invention

This invention relates to anticancer agents and the processes for their preparation.

The process of the invention for the preparation of N-{[5-(2,4-diamino-6-pteridinyl)ethyl]-2-theonyl}-L-glutamic acid (1) is illustrated in Scheme I and explained by Example 1., where the compound number identify the same compounds which they identify in all descriptions.

Cancer is a disease that is characterized by abnormal tissue growth and destruction and this acute or chronic disease of humans can be treated effectively with antifolate drugs such as methotrexate (MTX).

Methotrexate is a potent inhibitor of the enzyme dihydrofolate reductase, and thereby, it depletes the cells of various forms of the vitamin folic acid, that are required for cell division. Baugh, Krumdieck and Nair reported [Biochemical and Biophysical Research Communications 52:27 (1973)] that methotrexate is metabolized to its poly-y-glutamates in human tissues, and Nair and Baugh (Biochemistry 12, 3923, 1973) synthesized these metabolites and identified their presence in rodent tissues. Balinska, Galivan and Coward reported in Cancer Research that methotrexate poly-y-glutamates with higher chain lengths are retained longer within the cells (Cancer Res. 41:2751, 1981). Investigations of the biochemical pharmacology of methotrexate polyglutamates revealed beyond doubt that these metabolites are important determinants of anticancer activity and host toxicity. [M. G. Nair, in "Cancer Growth and Progression-Cancer Control in Man", Chapter 10, H. E. Kaiser (Ed.) Kluwer Academic Publishers, 1990); M. G. Nair, In "Chemistry of Antitumor Agents". D. E. V. Wilman (Ed), Blackie and Sons (Lond); Chapman and Hall (USA) Chapter 7 (1990)] Recently, several attempts have been made to reduce the host toxicity of methotrexate and other antifolates by modulating their glutamylation. (M. G. Nair, and Ann Abraham, U.S. Pat. No. 4,996,207 (1991); M. G. Nair, U.S. Pat. No. 5,073,554). In addition to the utility of classical antifolates as anticancer agents, they are also useful in the treatment of autoimmune diseases such as rheumatoid arthritis. Indeed, a close analogue of methotrexate (Rheumatrex), 10-deazaaminopterin (10-DAM) has been shown to be equally effective as an arthritis remittive drug for the treatment of rheumatoid arthritis in humans (C. L. Krumdieck, O. Castaneda, G. Alarcon, W. J. Koopman and M. G. Nair, U.S. Pat. No. 5,030,634) in a clinical trial. In this context, it was of interest to develop powerful inhibitors of dihydrofolate reductase with altered ability of polyglutamylation, and enhanced tissue penetration as better therapeutic agents for the treatment of neoplastic, autoimmune and inflammatory diseases. Substitution of the benzene ring of 10-deazaaminopterin [J. I. DeGraw, R. L. Kisliuk, Y. Gaumont, C. M. Baugh, and M. G. Nair, J. Med. Chem. 17, 552, (1973); M. G. Nair, J. Org. Chem. 50, 1879 (1985)] with a thiophene ring gave a very potent inhibitor of dihydrofolate reductase, that has demonstrated diminished polyglutamylation and enhanced transport to tumor cells as expected. This new thiophene substituted antifolate (1) and its close derivatives are envisioned to be anticancer and anti-inflammatory drugs exhibiting lower toxicity and enhanced specificity compared to methotrexate (MTX) and 10-deazaaminopterin (10-DAM). Although compound 1 is polyglutamylated less efficiently compared to methotrexate, it exhibits superior activity against the growth of ($I_{50}$ 10.2 vs 13.5 nM) human leukemia cells due to enhanced transport. Taken together, these new and unexpected results establish that compound 1 and its close analogues should have clinical utility as novel anticancer drugs capable of exhibiting lower host toxicity.

This invention accordingly provides a process for treating leukemia, ascitic and solid tumors and by analogy with methotrexate and 10-deazaaminopterin a process for treating auto-immune diseases such as rheumatoid arthritis and inflammatory diseases such as asthma, which comprises administering to a warm blooded animal with an abnormal proportion of leukocytes or other evidence of malignancy, rheumatoid arthritis, or asthma, a therapeutic nontoxic amount of N-{[5-(2,4-diamino-6-pteridinyl)ethyl]-2-theonyl}-L-glutamic acid (1) as such, or in the form of a pharmacologically acceptable salt thereof.

The salts of 1 may be formed with one or more of the amino groups of the pteridine ring with acids such as hydrochloric, hydrobromic, sulfuric, sulfonic, nitric, phosphoric, or organic carboxylic acids such as acetic, citric, salicylic, or methene sulfonic.

Compound 1 or salts thereof may be administered to a warm blooded animal by oral or parenteral (intraperitoneal, intravenous, intrathecal, subcutaneous, intramuscular, etc.) routes. Higher dosage of 1 may be administered in conjunction with racemic leucovorin [6-(R,S)5-formyltetrahydrofolate] or folic acid to further reduce toxicity in the treatment of cancer and auto-immune diseases such as rheumatoid arthritis.

The new thiophene substituted antifolate 1 may be provided in composite forms to facilitate administration to patients or in dosage unit form. A non-toxic and sterile carrier may be added to 1. This carrier may be a solid, liquid or semi-solid that may serve as a medium, vehicle or excipient. Methyl cellulose, polyhydroxybenzoate, talc, gelatin, lactose, dextrose, starch, mannitol, sorbitol, mineral oil, gum acacia, oil of theobroma or magnesium stearate may serve as the carriers. Compound 1 and carrier or diluent can be encapsulated, or enclosed in a paper or other container, cachet, gelatin, capsule or sachet when intended for use in dosage units.

The process of the invention for the preparation of 1 is a synthesis in which commercially available 2-thiophene carboxaldehyde is converted to the corresponding acetal derivative by reactions with a trialkyl orthoformate using standard procedures. The resulting 2-thiophene dialkyl acetal 5 is converted to a 2-carboxy-5-formylthiophene dialkyl acetal 6 by reacting with a strong base like butyllithium, lithium diisopropylamide (LDA) or potassium-t-butoxide followed by $CO_2$ in tetrahydrofuran at a temperature range of −60° to 30° C. Esterification of the carboxyl group of 6 to an ester followed by deprotection of the aldehyde gives the ester product, of 5-formyl thiophene-2-carboxyic acid 7. The above conversion of 6 to 7 can be accomplished by treating 6 with thionyl chloride in an appropriate alcohol for 12-24 hours and then stirring the reaction mixture with H$_2$O for 3 hours. 1-Phthalimido-3-(triphenylphosphoranylidine)-2-propanone(synthesized according to the literature procedure of (Nair, M. G., J. Org. Chem. 50, 1879, 1985) is refluxed in CH$_2$Cl$_2$ with 7 to prepare 4-(2-carbomethoxytheonyl)-1-pthalimido-3-buten-2-one (8). The enone 8 can be reduced to 1-phthalimido-4-(2-carbomethoxytheonyl)-2-butanone (9) by refluxing with palladium/carbon in formic acid/triethylamine mixture for 18 hr. This reaction can also be accomplished with Zn/CH$_3$COOH or by catalytic hydrogenation using catalysts such as Palladium or Platinum on carbon.

The ketone product (9) was protected as the oxime 1-Phthalimido-4-[(2-carbomethoxy)-5-theonyl]-2-butanone oxime (10) by standard procedure. The oxime was a mixture of syn and anti isomers. The isomeric mixture of the oxime was then subjected to hydrazinolysis following the literature procedure of Nair et al, (J. Org. Chem. 40, 1745, 1975) to obtain 1-amino-4-[(2-carbomethoxy)5-theonyl]-2-butanone oxime (11). Compound 11 was then reacted with 6-chloro-2,4-diamino-5-nitropyrimidine to obtain 1-[(2,4-diamino-5-nitropyrimidin-6-yl)amino]4-[(2carbomethoxy)-5-theonyl]-2-butanone oxime (12).

The next stage of synthesis is the conversion of 12 to 13, a procedure that involves the deprotection of the oxime mixture with a solution of TFA and 1N HCl, followed by reduction of the nitro group to the amino group by sodium dithionite in aqueous DMF. The resulting reduction product could then be cyclized with the use of inorganic aqueous base and oxidized with 5% KMnO$_4$ or by heating the reduction product in a solution of DMF to 100° C. for 1 h and subsequent hydrolysis to obtain 14.

The final stage of the synthesis is the coupling of a diester of L-glutamic acid such as diethyl-L-glutamate or di-t-butylglutamate to 14, first by converting 14 to the corresponding mixed anhydride with a suitable alkylchloroformate in THF or DMF in presence of a tertiary organic base and then reacting the resulting mixed anhdyride with the L-glutamate diester and subsequent workup. The product is then treated with a solution of inorganic base like sodium hydroxide or potassium hydroxide to obtain the sodium or porassium salt of compound 1. Acidification of the hydrolysate with acetic acid gives a precipitate of 1, which can be filtered and purified further.

Compound 1 is a potent inhibitor of L1210 dihydrofolate reductase (DHFR). DHFR inhibitory data for 1 and MTX under identical experimental conditions are shown in Table I.

TABLE I

| Inhibition of DHFR by 1 and MTX | |
|---|---|
| COMPOUND | I$_{50}$(nM) |
| 1 | 0.95 |
| MTX | 0.98 |

Compound 1 showed excellent inhibitory activity against the growth of CCRF-CEM human leukemia cells, and H35 hepatoma cells. (Table II). CCRF-CEM human leukemia cells (Table II) were more sensitive to 1 than methotrexate.

TABLE II

| Inhibition of tumor cell growth by 1 and methotrexate | | |
|---|---|---|
| | I$_{50}$(nM) | |
| Compound | CCRF-CEM Human leukemia | H35 hepatoma |
| 1 | 10.2 | 15 |
| Methotrexate | 13.5 | 10 |

Growth inhibition of H35 hepatoma cells was measured as described by Patil, Jones, Nair, Galivan, Maley, Kisliuk, Gaumont, Duch, and Ferone in the Journal of Medicinal Chemistry 32:1284 (1989) and that of CCRF-CEM human leukemia cells according to the procedures of McGuire, Graber, Licato, Vincenz, Coward, Nimec and Galivan (Cancer Research 49:4517, 1989).

The substrate activity of compound 1 as shown in Table III established that it is polyglutamylated. It has been shown previously that substrates of FPGS are capable of polyglutamylation in vivo and the relative magnitude of substrate activity of an antifolate to this enzyme compared to a standard is a measure of its relative ability to undergo polyglutamylation. The v/k values of Table III established that compound 1 is polyglutamylated less efficiently than either aminopterin or 10-deazaaminopterin.

TABLE III

| Substrate activity with CCRG-CEM human luekemia cell FPGS* | | | |
|---|---|---|---|
| COMPOUND | K$_m$(μM) | Vmax | V/K |
| Aminopterin | 4.6 | 100 | 21.7 |
| 10-DAM | 34.8 | 88.6 | 2.5 |
| 1 | 45.0 | 83.5 | 1.9 |

*Assay as described by McGuire, Bolanowska, and Piper in Biochem. Pharmacol 37; 3931, 1988.

Transport studies showed that compound 1 is transported more efficiently to H35 hepatoma cells in culture than methotrexate (TABLE IV). Transport influx was estimated by measuring the ability of 1 to complete with folinic acid transport to this cell line.

TABLE IV

| Inhibition of folinic acid transport to H35 hepatoma cells. | |
|---|---|
| COMPOUND | I$_{50}$(μM) |
| 1 | 5 |
| Methotrexate | 18 |

Transport experiments were conducted as described by Patil, Jones, Nair, Galivan, Maley, Kisliuk, Gaumont, Duch and Ferone in the Journal of Medicinal Chemistry 32: 1284 (1989). Folinic acid 2 μM, 15 min, uptake.

EXAMPLE 1

Ultraviolet spectra were obtained on a Bausch and Lomb Spectronic Model 2000 spectrophotometer interfaced with a Commodore Superpet computer. Melting points were determined on a Fisher Model 355 digital melting point analyzer. NMR spectra were run in CDCl$_3$ or CF$_3$COOH on a 90-MHz Perkin-Elmer Model R-32 spectrometer using Me$_4$Si as an internal standard unless otherwise specified. Field strength of the various proton resonances is expressed in parts per million and peak multiplicity is depicted as follows: s, singlet; d, doublet; t, triplet; q, quartet; c, unresolved multiplet, the center of which is given. HPLC analyses were performed on a Waters 600A multisolvent delivery system equipped with a Model 481 UV detector and Water 740 data module. Mass spectral analyses of final product were determined at University of South Alabama, Mass Spectrometry Center, Mobile, Ala.

2-Thiophene dimethyl acetal (5)

To a mixture of 11.2 gm (0.1 mole) of 2-thiophenecarboxaldehyde and 11.2 gm (0.105 mole) of trimethylorthoformate, was added a warm solution of 0.5 gm of ammonium bromide in 10 mL of dry methanol. After the reaction mixture was refluxed for 6 h, methanol was removed using rotary evaporator at room temperature and the resultant residue was vacuum distilled at 60° C. to obtain the desired product 5: Yield 11.37 gm (72%) NMR (CDCl$_3$) δ 7.4 (d, 1H, thiophene 3-H) 7.15 (m,2H,thiophene 4-H, thiophene 5-H) 3.45 (s,6H, CH$_3$O—).

2-Carboxy-5-formylthiophene dimethyl acetal (6)

To a solution of 6 gm (38 mmol) of 5 in 42 mL of dry THF was added 15.2 mL (38 mmol) of butyllithium (2.5M) in hexane at −60° C. The reaction mixture was kept stirring at −60° C. for 2 h and 5.4 gm of dry ice was added to the mixture at −40°. The solution kept stirring for 18 h at room temperature. The pH of the solution was adjusted to 5.5 and extracted with CH$_2$Cl$_2$. The CH$_2$Cl$_2$ layer was dried over Na$_2$SO$_4$. Removal of CH$_2$Cl$_2$ gave the light yellow product 6. Yield 4.9 gm (64%); mp 88°-90° C.; NMR. Anal. calcd for (C$_8$H$_{10}$O$_4$S) 2C, 47.52; H,4.95; S, 15.84. Found: C, 47.80; H, 4.64; S, 16.30.

Methyl 5-formylthiophene-2-carboxylate (7)

To a solution of 6 (500 mg, 2.5 mmol) in 10 mL of dry methanol was added 2 mL of SOCl$_2$ at 0° C. The reaction mixture was stirred for 18 h at room temperature, monitoring the reaction by TLC. After the starting material was consumed, 5 mL of dist. H$_2$O was added to the mixture and let stir for 3 to 4 h at room temperature. The reaction mixture was concentrated at 50° C. using a rotary evaporator and extracted with CH$_2$Cl$_2$. The CH$_2$Cl$_2$ layer was dried over Na$_2$SO$_4$ and filtered through a silica gel column. Removal of the solvent gave cream crystals of 7. Yield 400 mg (95%) mp 79° C.; MS m/z, 171 (MH+); calcd for (C$_7$H$_6$O$_3$S), 170. Anal. C,H,S. NMR (CDCl$_3$) δ7.89 (c,2H, thiophene 2H, thiophene 3-H) 4.05 (s,3H COOCH$_3$).

4-(2-carbomethoxytheonyl)-1-pthalimido-3-buten-2-one (8)

A mixture of 25.3 gm (54.7 mmol) of 1-phthalimido-3-(triphenylphosphoranylidene)-2-propanone and 9.3 gm (54.7 mmol) of 7 in CH$_2$Cl$_2$ was refluxed for 72 h. After cooling the solution to room temperature, 300 mL of methanol was added to it. On removal of CH$_2$Cl$_2$, white precipitate came out from the solution, which was filtered, washed with methanol and dried to obtain 8. Yield 17.6 gm (90.6%) mp 157°-158° C. NMR (CDCl$_3$) δ 7.95 (c,4H pthalimido) 6.8 (d,1H, olefinic) 4.78 (s,2H,CH$_2$) 3.95 (s,3H, COOCH$_3$). Anal. Calcd for C$_{18}$H$_{13}$NO$_5$S: C,60.84; H,3.66; N,3.94. Found C,60.37: H,3.83; N,3.78.

4-(2-Carbomethoxytheonyl)-2-pthalimido-2-butanone (9)

To a mixture of 5 gm (14.08 mmol) of 8 and 149.8 mg (0.1408 mmol) of 10% Pd/C was added 20.97 mL of triethylamine and 5.25 mL 95% formic acid. The reaction mixture was refluxed for 18 h at 100° C., poured over ice, triturated and filtered. The precipitate was washed with CH$_2$Cl$_2$, CH$_2$Cl$_2$ layer was dried over Na$_2$SO$_4$ and evaporated to dryness to get product 9. Yield 4.6 gm (89.5%) mp 131°-136° C. MS (m/z) 358 (MH+). NMR (CDCl$_3$) δ 8.05 (c,4H pthalimido) 4.75 (s, 2H, CH$_2$) 4.07 (s,3H, COOCH$_3$) 3.3 (m,4H,CH$_2$CH$_2$).

1-Phthalimido-4-(2-carbomethoxy-5-theonyl)-2-butanone oxime (10)

A mixture of 9 (4.6 gm, 12.6 mmol) and 1.3 gm hydroxylamine HCl in 350 mL of pyridine/MeOH (1:1) mixture was refluxed for 1 h, evaporated to dryness, triturated with 50 gm of ice and extracted with ethyl acetate. The ethyl acetate layer was dried over Na$_2$SO$_4$ and evaporated to dryness using a rotary evaporator to obtain the product 10, Yield 3.1 gm (66%), mp 125°-126°, NMR (CDCl$_3$) δ7.75 (c,5H, phthalimide, thiophene) 6.9 (d,1H, thiophene) 4.77, 4.45 (s,2H, CH$_2$) 3.9 (s,3H,COOCH$_3$) 3.1 (c,4H,CH$_2$CH$_2$) Anal. calcd for C$_{18}$H$_{16}$N$_2$O$_5$S:

1-Amino-4-(2-carbomethoxy-5-theonyl)-2-butanone oxime (11)

A solution of 10 (2.5 gm, 6.7 mmol) in 200 mL of methanol was made by warming to ~45° C. To this solution was added 0.45 mL of hydrazine in a N$_2$ atmosphere at room temperature and the mixture was stirred for 48 h. After all the starting material was consumed, reaction mixture was neutralized with 1N HCl and removed methanol was removed using a rotary evaporator under reduced pressure. To the residue was added 50 mL of H$_2$O, pH was adjusted to 4 with 1N HCl and filtered. The filtrate after adjusting the pH to 8.5 with NH$_4$OH was extracted with ethylacetate. The ethylacetate layer was dried over Na$_2$SO$_4$ and evaporated to dryness to obtain 11.

1-[(2,4-diamino-5-nitropyrimidin-6-yl)amino]-4-(2-carbomethoxy-5-theonyl)-2-butanone oxime (12)

The product 11 obtained from the hydrozynolysis of 2.5 gm of 10 was refluxed with 6-chloro-2,4-diamino-5-nitropyrimidine for 18 h, evaporated to dryness and triturated with 150 gm of ice. The yellow solid obtained was filtered and immediately used for the next step.

Conversion of 12 to the pteroic analogue 14

(a) Deprotection of oximes

The product 12 was dissolved in 30 mL of TFA (95%); kept in a 65° C. water bath and added 30 mL of 1NHCl during a period of 20 min. After the addition, the clear solution was evaporated to dryness, triturated with 100 g of ice, pH adjusted to 6.5 with solid NaHCO$_3$. The yellow precipitate of 13 was filtered and washed with water. UV (0.1N NaOH) λmax 337.4 nm.

(b) Dithionite reduction

The deprotected oxime 13 was dissolved in 350 mL of DMF by heating to ~90° C. To this solution was added 7.5 g of solid sodium dithionite at 65° C. 175 mL of water was added to the above mixture, followed by 7.5 g of sodium dithionite. During a period of 30 min, 175 mL of H$_2$O was added to the reaction mixture, keeping the temperature at 65° C. The resultant clear solution was concentrated to ~150 mL and 200 g of ice was added to it. The precipitate was filtered, washed with water and the UV spectrum (0.1N NaOH) showed a λmax at 279 nm.

(c) Cyclization, Hydrolysis and Oxidation to 14

The brown precipitate obtained from the dithionite reduction was dissolved in a mixture of 400 mL of 0.1N NaOH and 150 mL of CH$_3$CN and stirred at 25° C. for 18 hr. The pH of the reaction mixture was adjusted to 7.0 with 1N HCl, and the mixture was concentrated by rotary evaporation under reduced pressure to ~200 mL. To this concentrated solution was added 100 mL of MeOH followed by 12 mL of 5% KMnO$_4$ under stirring. After 30 min, the UV spectrum of the solution was checked for the appearance of a well defined λmax between 360 and 375 mm. Since the spectrum showed that the oxidation was complete, the solution was filtered, concentrated and the pH adjusted to 3.5–4 with glacial acetic acid. The yellow precipitate of 14, thus formed was filtered, washed with water and dried to obtain the crude product. The final purification was done by ion exchange chromatography over DEAE cellulose. NMR (TFA) ∂ 8.4 (s,1H,C$^7$H) 7.55, 6.65 (d,1H, thiophene) 3.25 (s,CH$_2$CH$_2$); MS (FAB) Calcd for (C$_{13}$H$_{12}$N$_6$O$_2$S.H)+317.0820706; Found (MH+)+317.084930.

N-{[5-(2,4-diamino-4-deoxy-6-pteridyl)ethyl]-2-theonyl}-L-glutamic acid (1)

A solution of 130 mg (0.4 mmol) of 13 in 15 mL of DMF was cooled to 0° C., followed by the addition of 0.09 mL (0.8 mmol) of N-methylmorpholine and 0.105 mL (0.8 mmol) of isobutylchloroformate. After 30 min stirring at 0° C., the solution was allowed to stir at 25° C. for 45 min and a solution of 240 mg (0.8 mmol) of diethyl-L-glutamate hydrochloride in 10 mL of DMF neutralized with 0.09 mL (0.8 mmol) of N-methylmorpholine was added to the activated pteroic analogue. The resultant mixture was stirred for 18 h at 25° C., evaporated to dryness under reduced pressure at 55° C. and the residue triturated with 50 g of crushed ice. The precipitated crude product was filtered and stirred for 18 h with a mixture of 40 mL of 0.1N NaOH and 15 mL of CH$_3$CN. The pH of the hydrolysate was adjusted to 7.5 with 1N HCl, and the solution was concentrated by rotary evaporation to ~10 mL, cooled and acidified with glacial HOAc to pH 3.5 and the resultant yellow precipitate was filtered, washed, and dried. The precipitate obtained was found to be a mixture of unreacted 13 and the desired product 1. The crude product was dissolved in 10 mL of 5% NH$_4$OH and evaporated under reduced pressure to a residue which was dissolved in 7 mL of distilled water and applied on a column of 10 g of C$_{18}$ silica gel that was equilibrated wit 10% CH$_3$CN in water. The product was eluted with 10% CH$_3$CN in water and the fraction containing the fast moving band on the column were pooled and the pH adjusted to 3.5 to precipitate product 1. The light yellow precipitate was separated by filtration, washed with water, and dried. Yield 85 mg (48%) UV (0.1N NaOH) λmax 256,(E=31,899) 368 (E=7725); MS (FAB). Calcd for (C$_{18}$H$_{19}$N$_7$O$_5$S.H)+ 446.1246639; Found (MH+), 446.124879.

Having regard to the foregoing disclosure, the following is claimed as inventive and patentable embodiments thereof:

1. N-{[5-(2,4-diamino-6-pteridinyl)ethyl]-2-theonyl}-L-glutamic acid having the following chemical structure:

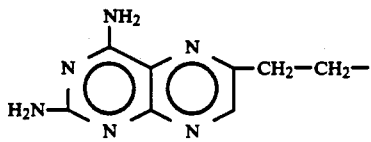

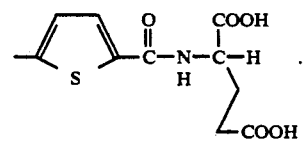

2. A compound having the following structure where R$^1$ and R$^2$ are hydrogen and R$^3$ is a methyl or ethyl group

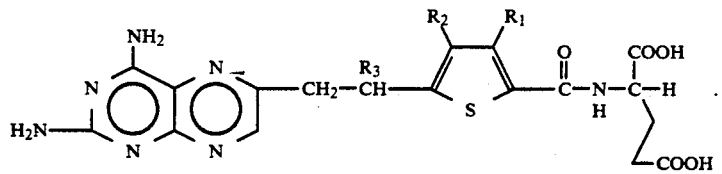

3. A pharmaceutical composition in dosage unit form for treating leukemia, ascites tumors or solid tumors comprising an amount within the range of about 0.1 to about 500 mg of N-{[5-(2,4-diamino-6-pteridinyl-ethyl]-2-theonyl}-L-glutamic acid per dosage unit therapeutically effective to ameliorate leukemia, ascites tumors or solid tumors together with a pharmaceutically acceptable nontoxic carrier or diluent thereof.

4. A process for treating leukemia, ascites tumors or solid tumors which comprises administrating orally or parenterally to a warm blooded animal having an abnormal proportion of leukocytes or other evidence of malignancy, a therapeutic and relatively non-toxic amount of N-{[5-(2,4-diamino-6-pteridinyl)ethyl]-2-theonyl}-L-glutamic acid (1) to ameliorate leukemia, ascites tumors or solid tumors.

* * * * *